(12) United States Patent
Van Der Beek et al.

(10) Patent No.: US 8,883,219 B2
(45) Date of Patent: Nov. 11, 2014

(54) NUTRITIONAL COMPOSITIONS WITH COATED LIPID GLOBULES

(75) Inventors: Eline Marleen Van Der Beek, Wageningen (NL); Gelske Speelmans, Wageningen (NL); Annemarie Oosting, Wageningen (NL); Antonie Van Baalen, Arnhem (NL); Marieke Abrahamse-Berkenveld, Heteren (NL); Günther Boehm, Leipzig (DE)

(73) Assignee: N. V. Nutricia, Zoetermeer (NL)

( * ) Notice: Subject to any disclaimer, the term of this patent is extended or adjusted under 35 U.S.C. 154(b) by 130 days.

(21) Appl. No.: 13/133,924

(22) PCT Filed: Dec. 11, 2009

(86) PCT No.: PCT/NL2009/050754
§ 371 (c)(1),
(2), (4) Date: Aug. 24, 2011

(87) PCT Pub. No.: WO2010/068103
PCT Pub. Date: Jun. 17, 2010

(65) Prior Publication Data
US 2011/0300225 A1    Dec. 8, 2011

(30) Foreign Application Priority Data
Dec. 11, 2008    (WO) ................ PCT/NL2008/050792

(51) Int. Cl.
| | | |
|---|---|---|
| A61K 9/16 | (2006.01) | |
| A61K 35/66 | (2006.01) | |
| A23L 1/30 | (2006.01) | |
| A61K 36/06 | (2006.01) | |
| A61K 35/20 | (2006.01) | |
| A61K 9/127 | (2006.01) | |
| A23L 1/29 | (2006.01) | |
| A61K 36/02 | (2006.01) | |
| A61K 35/60 | (2006.01) | |

(52) U.S. Cl.
CPC ............... *A61K 36/02* (2013.01); *A61K 35/66* (2013.01); *A23L 1/3006* (2013.01); *A61K 36/06* (2013.01); *A61K 35/20* (2013.01); *A61K 9/1276* (2013.01); *A23L 1/296* (2013.01); *A61K 35/60* (2013.01)
USPC ........................................ 424/498

(58) Field of Classification Search
None
See application file for complete search history.

(56) References Cited

U.S. PATENT DOCUMENTS

| | | | |
|---|---|---|---|
| 5,709,888 A | 1/1998 | Gil et al. | |
| 2002/0004527 A1 | 1/2002 | Auestad et al. | |
| 2003/0104078 A1 | 6/2003 | Barrett-Reis et al. | |
| 2004/0062820 A1 * | 4/2004 | Lasekan et al. | 424/682 |
| 2005/0037089 A1 * | 2/2005 | Jobbins | 424/602 |
| 2005/0214392 A1 | 9/2005 | McPeak et al. | |
| 2006/0188614 A1 | 8/2006 | Shapira | |
| 2006/0210697 A1 | 9/2006 | Mower | |
| 2007/0073193 A1 | 3/2007 | Park | |
| 2007/0073194 A1 | 3/2007 | Chen et al. | |
| 2008/0064656 A1 | 3/2008 | Van Tol | |
| 2008/0292724 A1 | 11/2008 | Hageman et al. | |
| 2009/0011075 A1 | 1/2009 | Shulman et al. | |
| 2011/0300204 A1 | 12/2011 | Van Der Beek et al. | |

FOREIGN PATENT DOCUMENTS

| | | | |
|---|---|---|---|
| EP | 0 333 288 A1 | | 9/1989 |
| EP | 1 252 824 A2 | | 10/2002 |
| EP | 1 800 675 A1 | | 6/2007 |
| JP | 2001-158736 | * | 11/1999 |
| SU | 1084006 A | | 4/1984 |
| WO | WO-03/005836 A2 | | 1/2003 |
| WO | WO-2005/007373 A1 | | 1/2005 |
| WO | WO-2005/051091 A1 | | 6/2005 |
| WO | WO-2005/051092 A2 | | 6/2005 |
| WO | WO-2006/052134 A2 | | 5/2006 |
| WO | WO-2006/094995 A1 | | 9/2006 |
| WO | WO-2006/114790 A2 | | 11/2006 |
| WO | WO-2007/073192 A2 | | 6/2007 |
| WO | WO-2007/073193 A2 | | 6/2007 |
| WO | WO-2007/073194 A2 | | 6/2007 |
| WO | WO-2007/097523 A2 | | 8/2007 |
| WO | WO-2008/005033 A1 | | 1/2008 |
| WO | WO-2008/081934 A1 | | 7/2008 |
| WO | WO-2009/051502 A1 | | 4/2009 |
| WO | WO-2009/057121 A1 | | 5/2009 |
| WO | WO-2009/066685 A1 | | 5/2009 |
| WO | WO-2009/138680 A2 | | 11/2009 |
| WO | WO-2009/154448 A1 | | 12/2009 |
| WO | WO-2010/027258 A1 | | 3/2010 |
| WO | WO-2010/027259 A1 | | 3/2010 |
| WO | WO-2010/068086 A1 | | 6/2010 |
| WO | WO-2010/068103 A1 | | 6/2010 |
| WO | WO-2010/068105 A1 | | 6/2010 |
| WO | WO-2011/108934 A1 | | 9/2011 |

OTHER PUBLICATIONS

Database WPI Week 200937, Thomoson Scientific, London, GB, AN 2009-J69887, XP002578379.
Michalski, et al., "Size Distribution of Fat Globules in Human Colostrum, Breast Milk, and Infant Formula", Journal of Dairy Science, vol. 88, 2005, pp. 1927-1940, American Dairy Science Association, XP002505628.
Search Report in International Application PCT/NL2009/050754 dated May 7, 2010.

(Continued)

*Primary Examiner* — Snigdha Maewall
(74) *Attorney, Agent, or Firm* — Gilberto M. Villacorta; Sunit Talapatra; Foley & Lardner LLP

(57) ABSTRACT

The present invention relates to a nutritional composition for infants and/or toddlers comprising a lipid component which has a lipid globules coated with phospholipids. The composition is used for increasing bone mineral content, bone mineral density, preventing osteoporosis, and/or preventing ostopenia.

17 Claims, No Drawings

(56) References Cited

OTHER PUBLICATIONS

Search Report in International Application No. PCT/NL2009/050756 dated May 11, 2010.
Agostoni et al., "Polyunsaturated Fatty Acids in Human Milk and Neurological Development in Breastfed Infants," Current Pediatric Reviews, vol. 1, pp. 25-30, XP002643794 (2005).
Benoit et al., "Phospholipid Species and Minor Sterols in French Human Milks," Food Chemistry, 120:684-691 (2010).
Hamilton, "Interactions of Triglycerides with Phospholipids; Incorporation into the Bilayer Structure and Formation of Emulsions," 28, Biochem, 2514-2520 (1989).
Holman et al., "Deficiency of essential fatty acids and membrane fluidity during pregnancy and lactation", Proceedings of the National Academy of Sciences of the United States of America, vol. 88, No. 11, Jun. 1, 1991, pp. 4835-4839, XP002620898.
Hur et al., "Influence of initial emulsifier type on microstructurel changes occurring in emulsified lipids during in vitro digestion," Food Chemistry, vol. 114, pp. 253-262, XP002607759 (2009).
International Preliminary Report on Patentability for PCT/NL2011/050156—mailed Aug. 24, 2012.
International Preliminary Report on Patentability for PCT/NL2011/050187—mailed Jun. 13, 2012.
International Preliminary Report on Patentability for PCT/NL2011/050188—mailed Jun. 15, 2012.
International Preliminary Report on Patentability mailed Jul. 19, 2010 in PCT/NL2009/050343.
International Search Report for PCT/NL2009/050525, mailed Dec. 1, 2009 (3 pages).
International Search Report for PCT/NL2011/050156—mailed Jun. 1, 2011.
International Search Report for PCT/NL2011/050187—mailed Jul. 5, 2011.
International Search Report for PCT/NL2011/050188—mailed Jul. 5, 2011.
International Search Report mailed Dec. 14, 2009 in Application No. PCT/NL2009/050526.
International Search Report mailed Jul. 15, 2009 in PCT/NL2009/050343.
Jensen et al., "Specialty Lipids for Infant Nutrition. I. Milks and Formulas," Journal of Pediatric Gastroenterlogy and Nutrition, vol. 15, No. 3, pp. 232-245, XP002620897 (1992).
Joscelyne et al., "Food Emulsions Using Membrane Emulsification; Conditions for Producing Small Droplets," vol. 39, Journal of Food Engineering. pp. 59-64 (1999).
Makrides et al., "Fatty acid composition of brain, retina, and erythrocytes in breast- and formula-fed infants," American Journal of Clinical Nutrition, US, vol. 60, No. 2, 1994, pp. 189-194, XP002620896.

Michalski et al., "Optical parameters of milk fat globules for laser light scattering measurements," Lait, 2001, 81(6):787-796.
Michalski et al., "The Dispersion State of Milk Fat Influences Triglyceride Metabolism in the Rat," European Journal of Nutrition, 44:436-444 (2005).
Michalski et al., "The Supramolecular Structure of Milk Fat Influences Plasma Triacylglycerols and Fatty Acid Profile in the Rat," European Journal of Nutrition, 45:215-224 (2006).
Mun et al., "Influence of interfacial composition on in vitro digestibility of emulsified lipids: potential mechanism for chitosan's ability to inhibit fat digestion," Food Biophysics, vol. 1, pp. 21-29, XP002607758 (2006).
Osteoporosis, PubMed Health, available at http;www.ncbi.nlm.nih.gov/pubmedhealth/PMH0001400, 2012.
Park et al., "Influence of encapsulation of emulsified lipids with chitosan on their in vivo digestibility," Food Chemistry, vol. 104, pp. 761-767, XP002607757 (2007).
Vickers, et al., "Supplementation with a Mixture of Complex Lipids Derived from Milk to Growing Rats Results in Improvements in Parameters Related to Growth and Cognition," Nutrition Research, 29:426-435 (2009).
Durand, A. et al. "Particle sizes and stability of UHT bovine, cereal and grain milks", Food Hydrocolloids, 2003, vol. 17, pp. 671-678.
Fave, G. et al. "Physicochemical properties of lipids; New strategies to manage fatty acid bioavailability", Cellular and Molecular Biology, 2004, vol. 50, No. 7, pp. 815-831.
McClements, D. "Food Emulsions—Principles, Practices, and Techniques", CRC Press, Second Edition, 2005, Section 7.3.
Michalski, M. et al. "Size Distribution of Fat Globules in Human Colostrum, Breast Milk, and Infant Formula", J. Dairy Sci., 2005, vol. 88, pp. 1927-1940.
Petrowski, G. "Emulson stability and its relation to foods", Emulsion Stability, 1976, pp. 309-359.
Ruegg, et al. "The Fat globule size distribution in human milk", Biochimica et Biophysica Acta, 1981, vol. 666., pp. 7-14.
Schultz, S. et al. "High-Pressure homogenization as a process for emulsion formation", Chem. Eng. Technol., 2004, vol. 27, No. 4, pp. 361-368.
Simonin, C. et al. "Comparison of the fat content and fat globule size distribution of breast milk from mothers delivering term and preterm", The American Journal of Clinical Nutrition, Oct. 1984, vol. 40, pp. 820-826.
Whittlestone, W. et al. "Variations in the Fat Content of Human Milk During Suckling", Ruakura Animal Research Station, Department of Agriculture, pp. 204-206.
Lucas Alan, "Long-Term Programming Effects of Early Nutrition—Implications for the Preterm Infant", Journal of Perinatology (2005) 25, S2-S6.
InFat™—The premium choice for infant formula-closer to mother's milk, Nov. 2009, AAK Magazine.

\* cited by examiner

NUTRITIONAL COMPOSITIONS WITH COATED LIPID GLOBULES

FIELD OF THE INVENTION

The invention relates to the field of infant milk formula and growing up milks for improving bone health.

BACKGROUND

Breast-feeding is the preferred method of feeding infants. However, there are circumstances that make breast-feeding impossible or less desirable. In those cases infant formulae are a good alternative. The composition of modern infant formulae is adapted in such a way that it meets many of the special nutritional requirements of the fast growing and developing infant.

However, differences between breast feeding and feeding infant formulae exist. Breastfeeding in early life is associated with higher bone mass density and bone mineral content later in life during childhood and early adolescence compared with those who were bottle-fed. The implication of this observation is that osteoporosis prevention programs need to start very early in the life cycle. Adult degenerative bone disease (osteoporosis), a major public health problem in the West, has been linked to peak bone mass attained in young adult life. Following attainment of peak bone mass, bone mineral content falls and may descend below the safety level for clinical disease. Most interventions to reduce the incidence of clinical disease have been in middle life.

Human milk is the major source of energy for many infants during the first part of their lives. It has a high content of the saturated fatty acid palmitic acid (20-25%), which is primarily located in the sn-2 position of the triacylglycerols (~70%). The n-1, 3 positions of vegetable fats, normally used in infant formulae, are rich in saturated fatty acids such as palmitate and stearate and are not appropriate to be used in infant nutrition. The triglycerides are digested in the infant by lipases which release the sn-1, 3 fatty acids. When these palmitic- and stearic acids are released from vegetable triglycerides they tend to create salts of dietary calcium. Calcium salts of saturated fatty acids are insoluble and tend to precipitate and to be secreted from the body. This results in the loss of crucial calcium. Formation of calcium soaps causes loss in faeces of energy as well as of calcium, and this loss can be so high that it can influence bone mineralization, i.e. normal skeletal and bone development of the infant, as well as other aspects of normal health and development in infants. Hence, advanced infant formulas include synthetically structured fats produced to mimic the unique structure and characteristics of human milk fat. Such structured fats include Betapole or InFat which provide 22% total palmitic acid of which 43% is at the sn-2 position and 25% palmitic acid, up to 68% of which are at the sn-2 position, respectively.

WO 2005/07373 relates to compositions comprising such synthetically structured triglycerides with high levels of mono- or polyunsaturated fatty acids at positions sn-1 and sn-3 of the glycerol backbone, for use in enhancing calcium absorption and in the prevention and/or treatment of disorders associated with depletion of bone calcium and bone density, prevention and treatment of osteoporosis, for the enhancement of bone formation and bone mass maximization and for the enhancement of bone formation in infants and young children.

WO 2007/097523 aims to provide a fat composition as a human milk substitute comprising a diglyceride in which unsaturated fatty acids are bonded in the 1,2-positions or 1,3-positions and a triglyceride containing a large amount of palmitic acid or stearic acid as a saturated fatty acid in the 2-position of the triglyceride.

WO 2005/051092 concerns a lipid preparation comprising a combination of phosphatidylcholine (PC), phosphatidylethanolamine (PE), phosphatidylserine (PS) and phosphatidylinositol (PI), wherein the quantitative ratio between these glycerophospholipids essentially mimics their corresponding ratio in naturally occurring human milk fat.

Other infant formulae reduce the amount of palmitic acid to levels lower than that observed in human milk. EP 1252824 relates to a method for increasing the bone mineralization of an infant or toddler, comprises administering to said human a source of calcium and a fat blend that is low in palmitic acid.

SUMMARY OF THE INVENTION

The inventors surprisingly found that when the diet administered during early life comprises lipid globules which are coated with a layer comprising phospholipids the body composition later in life is affected. Coating lipid globules in infant diet results in an increased bone mineral content (BMC) and increased bone mass density (BMD) which was maintained later in life. This effect was surprisingly accompanied by a decreased fat mass, decreased relative fat mass and/or decreased obesity later in life. These results were not or to a much lesser degree observed when the phospholipids were added separately from the lipid globules to the diet.

The important difference between the formulae was the coating of the lipid globules with phospholipids, whereas the fatty acid profile was similar in the formulae and the amount of palmitic and stearic acid present at sn-1 and sn-3 positions in the fat was also similar. Both formulae further enabled a similar good growth and development early in life. Surprisingly the increase in BMD and/or BMC remained later in life when both groups received the same diet for a long period, indicating that early nutrition has an effect on BMD and/or BMC extending beyond the period in which it is actually administered. Early diet of the present invention has a programming effect on BMD and/or BMC. An even improved effect on BMC and/or BMD, and fat mass relative to total body mass later in life was observed when the lipid globules coated by an outer layer of phospholipids were enlarged in size.

Standard infant milk formulae have vegetable fat as lipid component. The lipid is homogenized in order to create a stable emulsion and the lipid globules are small, with a volume-weighted mode diameter in the range of about 0.3-0.6 μm. Typically, phospholipids are not specifically added, but small amounts may be present in ready-to-drink formula for stability reasons. It was found that the lipid globules of standard, e.g. prepared from powdered, infant formulas are covered with milk proteins and not with phospholipids. It is assumed that these proteins are in particular casein.

The present invention relates to infant formulae or growing up milks for toddlers comprising vegetable fats with lipid globules coated by phospholipids. This can be achieved upon homogenizing the lipid component comprising vegetable fat in the presence of phospholipids, before a drying step.

It has now surprisingly been found that the coating of the lipid globule administered early in life is one of the determinative factors which affect body composition, in particular bone mineral content and bone mass density and/or lean body mass, later in life. The present invention therefore can be used for food compositions intended for infants and/or toddlers in order to increase bone mineral content and/or increase bone mass density. The present invention therefore can be used for food compositions intended for infants and/or toddlers in order to prevent or reduce the risk for osteoporosis later in life, for the enhancement of bone formation and bone mass maximization and for the enhancement of bone formation in infants and young children.

The present invention also allows to formulate infant milk formulae with high levels of palmitic and stearic acid, as observed in human milk and with the use of natural lipids, i.e. without the use of synthetically made triglycerides, which are more expensive and subject to strict food legislations. The use of the synthetically made lipids with palmitic acid in the sn-2 position has the additional disadvantage of having direct diet effects regarding body weight, lean body mass and increasing fat mass. Surprisingly, it was found that while increasing BMD and BMC, advantageously fat mass and relative fat mass was decreased later in life using the lipid globules of the present invention.

DETAILED DESCRIPTION

The present invention thus concerns a method for
increasing bone mass density and/or increasing bone mineral content and/or
preventing osteoporosis and/or osteopenia
said method comprising administering to a human subject a nutritional composition comprising 10 to 50 wt. % vegetable lipids based on dry weight of the composition and 1.0 to 20 wt. % phospholipids based on total lipid and said composition comprising lipid globules with a core comprising said vegetable lipids and a coating comprising said phospholipids.

The present invention can also be worded as the use of lipid for the manufacture of a nutritional composition for use in increasing bone mass density and/or increasing bone mineral content, said nutritional composition comprising 10 to 50 wt. % vegetable lipids based on dry weight of the composition and 1.0 to 20 wt. % phospholipids based on total lipid, and said composition comprising lipid globules with a core comprising said vegetable lipids and a coating comprising said phospholipids.

The present invention can also be worded as the use of lipid for the manufacture of a nutritional composition for use in preventing osteoporosis and/or osteopenia, said nutritional composition comprising 10 to 50 wt. % vegetable lipids based on dry weight of the composition and 1.0 to 20 wt. % phospholipids based on total lipid, and said composition comprising lipid globules with a core comprising said vegetable lipids and a coating comprising said phospholipids.

The present invention can also be worded as a nutritional composition comprising 10 to 50 wt. % vegetable lipids based on dry weight of the composition and 1.0 to 20 wt. % phospholipids based on total lipid, said composition comprising lipid globules with a core comprising said vegetable lipids and a coating comprising said phospholipids, for use in increasing bone mass density and/or increasing bone mineral content.

The present invention can also be worded as a nutritional composition comprising 10 to 50 wt. % vegetable lipids based on dry weight of the composition and 1.0 to 20 wt. % phospholipids based on total lipid, said composition comprising lipid globules with a core comprising said vegetable lipids and a coating comprising said phospholipids, for use in preventing osteoporosis and/or osteopenia.

Thus for sake of clarity it is noted that the lipid globules comprising a coating are formed from the vegetable lipids and phospholipids. Thus in one embodiment the lipid in the nutritional compositions in the method or use according to the present invention is present in the form of lipid globules with a core comprising said vegetable lipids and a coating comprising said phospholipids. Preferably essentially all the lipid in the nutritional compositions in the method or use according to the present invention is present in the form of lipid globules with a core comprising said vegetable lipids and a coating comprising said phospholipids Bone Mass Density, Bone Mineral Content, Osteoporosis The present composition is preferably administered to a human subject with an age below 36 months, preferably below 18 months, more preferably below 12 months, even more preferably below 6 months.

Bone mass density (BMD) refers to the amount of matter per cubic centimeter of bones. Herein the term "bone mass" refers to the mass of bone mineral. In adults a low BMD is a strong predictor for osteoporosis and/or osteopenia. In infants a higher BMD is related to increased length, and lower risk fracture. Early optimal growth is predicting increased length in adulthood. Bone mineral content (BMC) refers to bone mineral content as a measure of bone strength. During growth BMC is a more relevant parameter than BMD, because it factors out most of the component of bone accumulation that is associated with change in bone size. So, in infancy, when assessing bone parameters, BMC is the more relevant parameter.

The terms "bone mineralization" and "bone mass accretion" are being used interchangeably within this application. Thus within the present specification and claims, they should be considered as synonyms. "Bone mineralization" should also be considered synonymous with increasing, enhancing or improving "bone strength", "bone mineral density", "bone mineral content", "bone mass", "bone accretion", etc.

BMD and BMC are typically determined by ultrasound, radiographic absorptiometry, single energy X-ray absorptiometry (SXA), peripheral dual energy X-ray absorptiometry (PDXA, dual energy X-ray absorptiometry (DEXA), single photon absorptiometry (SPA), dual energy radioactive photon absorptiometry (DPA) and quantitative computerized tomography (QCT). Preferably BMD and/or BMC is measured by DEXA.

In the context of this invention, increase in BMD is defined as an increase of at least 2%, preferably at least 4%, when compared to a control not receiving the nutrition of the present invention. For example as determined in a comparative study in an animal model as described in example 2.

In the context of this invention, increase in BMC is defined as an increase of at least 5%, preferably at least 7%, when compared to a control not receiving the nutrition of the present invention. For example as determined in a comparative study in an animal model as described in example 2.

The term "osteopenia," as used herein, refers to decreased bone mass below a threshold that compromises the structural integrity of the skeletal bone. An 'osteopenic' condition is a condition in which the bone mass density is decreased compared to a young normal control value. "Young normal" known as the "T-score" compares BMD to optimal or peak density of a 30-year old healthy adult and determines the fracture risk, which increases as BMD falls below young normal levels. The World Health Organization (WHO) has set the values for interpreting T-scores and defined osteoporosis and osteopenia based on these values: Osteopenia, on the other hand, is defined as a T-score between −1 and −2.5.

Osteoporosis is a disease of bone that leads to an increased risk of fracture. In osteoporosis the bone mass density (BMD) is reduced, bone microarchitecture is disrupted, and the amount and variety of non-collageneous proteins in bone is altered. Osteoporosis is defined by the World Health Organization (WHO) as a bone mass density with a T-score below −2.5.

Obesity

Obesity in the present invention relates to an excess of body fat mass. Fat mass is also known as adipose tissue or fat tissue. An adult human person suffers from obesity if over 25 wt. % (for man) or over 30 wt. % (for women) of body weight is fat mass. Obesity is sometimes referred to as adiposity.

Suitable ways to determine % body fat mass are underwater weighing, skin fold measurement, bioelectrical impedance analysis, computed tomography (CT/CAT scan), magnetic resonance imaging (MRI/NMR), ultrasonography and dual energy X-ray absorptiometry (DEXA). A preferred method is DEXA measurement. In the context of this invention body fat mass is determined by DEXA.

Lipid Component

The present composition comprises lipid. The lipid provides preferably 30 to 60% of the total calories of the composition. More preferably the present composition comprises lipid providing 35 to 55% of the total calories, even more preferably the present composition comprises lipid providing 40 to 50% of the total calories. When in liquid form, e.g. as a ready-to-feed liquid, the composition preferably comprises 2.1 to 6.5 g lipid per 100 ml, more preferably 3.0 to 4.0 g per 100 ml. Based on dry weight the present composition preferably comprises 10 to 50 wt. %, more preferably 12.5 to 40 wt. % lipid, even more preferably 19 to 30 wt. % lipid.

Lipids include polar lipids (such as phospholipids, glycolipids, sphingomyelin, and cholesterol), monoglycerides, diglycerides, triglycerides and free fatty acids. Preferably the composition comprises at least 75 wt. %, more preferably at least 85 wt. % triglycerides based on total lipids.

The lipid of the present invention comprises vegetable lipids. The presence of vegetable lipids advantageously enables an optimal fatty acid profile, high in (poly)unsaturated fatty acids and/or more reminiscent to human milk fat. Using lipids from cow's milk alone, or other domestic mammals, does not provide an optimal fatty acid profile. This less optimal fatty acid profile, such as a large amount of saturated fatty acids, is known to result in increased obesity. Preferably the present composition comprises at least one, preferably at least two lipid sources selected from the group consisting of linseed oil (flaxseed oil), rape seed oil (such as colza oil, low erucic acid rape seed oil and canola oil), salvia oil, perilla oil, purslane oil, lingonberry oil, sea buckthorn oil, hemp oil, sunflower oil, high oleic sunflower oil, safflower oil, high oleic safflower oil, olive oil, black currant seed oil, echium oil, coconut oil, palm oil and palm kernel oil. Preferably the present composition comprises at least one, preferably at least two lipid sources selected from the group consisting of linseed oil, canola oil, coconut oil, sunflower oil and high oleic sunflower oil. Commercially available vegetable lipids are typically offered in the form a continuous oil phase. When in liquid form, e.g. as a ready-to-feed liquid, the composition preferably comprises 2.1 to 6.5 g vegetable lipid per 100 ml, more preferably 3.0 to 4.0 g per 100 ml. Based on dry weight the present composition preferably comprises 10 to 50 wt. %, more preferably 12.5 to 40 wt. % vegetable lipid, even more preferably 19 to 30 wt. %. Preferably the composition comprises 50 to 100 wt. % vegetable lipids based on total lipids, more preferably 70 to 100 wt. %, even more preferably 75 to 97 wt. %. It is noted therefore that the present composition also may comprise non-vegetable lipids. Suitable and preferred non-vegetable lipids are further specified below.

Phospholipids

The present invention comprises phospholipids. Phospholipids belong to the group of polar lipids. Polar lipids are amphipathic of nature and include glycerophospholipids, glycosphingolipids, sphingomyelin and/or cholesterol. The composition comprises phospholipids (the sum of glycerophospholipids and sphingomyelin). Polar lipids in the present invention relate to the sum of glycerophospholipids, glycosphingolipids, sphingomyelin and cholesterol. According to the present invention phospholipids and optionally other polar lipids are present as a coating of the lipid globule. By 'coating' is meant that the outer surface layer of the lipid globule comprises phospholipids and optionally other polar lipids, whereas these polar lipids are virtually absent in the core of the lipid globule. The presence of phospholipids and optionally other polar lipids as a coating or outer layer of the lipid globule in the diet administered early in life was found to advantageously increase BMC and/or BMD later in life.

The present composition preferably comprises glycerophospholipids. Glycerophospholipids are a class of lipids formed from fatty acids esterified at the hydroxyl groups on carbon-1 and carbon-2 of the backbone glycerol moiety and a negatively-charged phosphate group attached to carbon-3 of the glycerol via an ester bond, and optionally a choline group (in case of phosphatidylcholine, PC), a serine group (in case of phosphatidylserine, PS), an ethanolamine group (in case of phosphatidylethanolamine, PE), an inositol group (in case of phosphatidylinositol, PI) or a glycerol group (in case of phosphatidylglycerol, PG) attached to the phosphate group. Lysophospholipids are a class of phospholipids with one fatty acyl chain. Preferably the present composition contains PC, PS, PI and/or PE, more preferably at least PC.

The present composition preferably comprises glycosphingolipids. The term glycosphingolipids as in the present invention particularly refers to glycolipids with an amino alcohol sphingosine. The sphingosine backbone is O-linked to a charged headgroup such as ethanolamine, serine or choline backbone. The backbone is also amide linked to a fatty acyl group. Glycosphingolipids are ceramides with one or more sugar residues joined in a β-glycosidic linkage at the 1-hydroxyl position. Preferably the present composition contains gangliosides, more preferably at least one ganglioside selected from the group consisting of GM3 and GD3.

The present composition preferably comprises sphingomyelin. Sphingomyelins have a phosphorylcholine or phosphorylethanolamine molecule esterified to the 1-hydroxy group of a ceramide. They are classified as phospholipid as well as sphingolipid, but are not classified as a glycerophospholipid nor as a glycosphingolipid.

Sphingolipids are in the present invention defined as the sum of sphingomyelin and glycosphingolipids. Phospholipids are in the present invention defined as the sum of sphingomyelin and glycerophospholipids. Preferably the phospholipids are derived from milk lipids. Preferably the weight ratio of phospholipids:glycosphingolipids is from 2:1 to 10:1, more preferably 2:1 to 5:1.

The present composition comprises phospholipids. Preferably the present composition comprises 1.0 to 20 wt. % phospholipids based on total lipid, more preferably 1.0 to 10 wt. %, even more preferably 2 to 10 wt. % even more preferably 3 to 8 wt. % phospholipids based on total lipid. Preferably the present composition comprises 0.1 to 10 wt. % glycosphingolipids based on total lipid, more preferably 0.5 to 5 wt. %, even more preferably 2 to 4 wt %. Preferably the present composition comprises 1.1 to 10 wt. % (glycosphingolipids plus phospholipids) based on total lipid.

The present composition preferably comprises cholesterol. The present composition preferably comprises at least 0.005 wt. % cholesterol based on total lipid, more preferably at least 0.02 wt. %, more preferably at least 0.05 wt. %., even more preferably at least 0.1 wt. %. Preferably the amount of cholesterol does not exceed 10 wt. % based on total lipid, more preferably does not exceed 5 wt. %, even more preferably does not exceed 1 wt. % of total lipid.

Preferably the present composition comprises 1.0 to 25 wt. % polar lipids based on total lipid, wherein the polar lipids are the sum of phospholipids, glycosphingolipids, and cholesterol, more preferably 1.5 to 12 wt. %, more preferably 1.0 to 10 wt. %, even more preferably 2 to 10 wt %, even more preferably 3.0 to 10 wt. % polar lipids based on total lipid, wherein the polar lipids are the sum of phospholipids, glycosphingolipids, and cholesterol.

Preferred sources for providing the phospholipids, glycosphingolipids and/or cholesterol are egg lipids, milk fat, buttermilk fat and butter serum fat (such as beta serum fat). A preferred source for phospholipids, particularly PC, is soy lecithin and/or sunflower lecithin. The present composition preferably comprises phospholipids derived from milk. Preferably the present composition comprises phospholipids and glycosphingolipids derived from milk. Preferably also cholesterol is obtained from milk. Preferably the polar lipids are derived from milk. Polar lipids derived from milk include the polar lipids isolated from milk lipid, cream lipid, butter serum lipid (beta serum lipid), whey lipid, cheese lipid and/or buttermilk lipid. The buttermilk lipid is typically obtained during the manufacture of buttermilk. The butter serum lipid or beta serum lipid is typically obtained during the manufacture of anhydrous milk fat from butter. Preferably the phospholipids, glycosphingolipids and/or cholesterol are obtained from milk cream. The composition preferably comprises phospholipids, glycosphingolipids and/or cholesterol from milk of cows, mares, sheep, goats, buffalos, horses and camels. It is most preferred to use a lipid extract isolated from cow's milk. The use of polar lipids from milk fat advantageously comprises the polar lipids from milk fat globule membranes, which are more reminiscent to the situation in human milk. Polar lipids derived from fat milk advantageously decrease fat mass to a larger extent than polar lipids from other sources. The polar lipids are located on the surface of the lipid globule, i.e. as a coating or outer layer. A suitable way to determine whether the polar lipids are located on the surface of the lipid globules is laser scanning microscopy as given in example 1. The concomitant use of polar lipids derived from domestic animals milk and trigycerides derived from vegetable lipids therefore enables to manufacture coated lipid globules with a coating more similar to human milk, while at the same time providing an optimal fatty acid profile. Suitable commercially available sources for milk polar lipids are BAEF, SM2, SM3 and SM4 powder of Corman, Salibra of Glanbia, and LacProdan MFGM-10 or PL20 from Arla. Preferably the source of milk polar lipids comprises at least 4 wt. % phospholipids based on total lipid, more preferably 7 to 75 wt. %, most preferably 20 to 70 wt. % phospholipids based on total lipid. Preferably the weight ratio phospholipids to protein is above 0.10, more preferably above 0.20, even more preferably above 0.3. Preferably at least 25 wt. %, more preferably at least 40 wt. %, most preferably at least 75 wt. % of the polar lipids is derived from milk polar lipids.

Fatty Acid Composition

Herein LA refers to linoleic acid and/or acyl chain (18:2 n6); ALA refers to α-linolenic acid and/or acyl chain (18:3 n3); LC-PUFA refers to long chain polyunsaturated fatty acids and/or acyl chains comprising at least 20 carbon atoms in the fatty acyl chain and with 2 or more unsaturated bonds; DHA refers to docosahexaenoic acid and/or acyl chain (22:6, n3); EPA refers to eicosapentaenoic acid and/or acyl chain (20:5 n3); ARA refers to arachidonic acid and/or acyl chain (20:4 n6); DPA refers to docosapentaenoic acid and/or acyl chain (22:5 n3); PA refers to palmitic acid and/or acyl chain (16:0); SA refers to stearic acid and/or acyl chain (18:0).

Preferably the composition comprises PA and/or SA. PA is a major component of human milk lipids. Preferably the composition comprises at least 16 wt. %, more preferably at least 19 wt. % based on total fatty acids, even more preferably at least 20 wt. %. Preferably the composition comprises less than 35 wt. % based on FA, more preferably less than 30 wt. %. A too high content of PA results in excessive calcium soap formation and has a negative effect on BMD and/or BMC. Preferably the palmitic acid in the lipids is for over 75 wt. %, more preferably 90 wt. % in the sn-1 or sn-3 position. The present invention also allows to formulate infant milk formulae with high levels of palmitic and stearic acid, as observed in human milk and with the use of natural lipids, i.e. without the use of synthetically made triglycerides with PA or SA on the sn-2 position, which are more expensive and subject to strict food legislations. The use of the synthetically made lipids with palmitic acid in the sn-2 position has the additional disadvantage of having direct diet effects by increasing body weight, lean body mass and fat mass early in life.

A high weight ratio of dietary LA to ALA is associated with a lower bone mass density. Therefore, LA preferably is present in a sufficient amount in order to promote a healthy growth and development, yet in an amount as low as possible to prevent a decrease in BMD. The composition therefore preferably comprises less than 15 wt. % LA based on total fatty acids, preferably between 5 and 14.5 wt. %, more preferably between 6 and 10 wt. %. Preferably the composition comprises over 5 wt. % LA based on fatty acids. Preferably ALA is present in a sufficient amount to promote a healthy growth and development of the infant. The present composition therefore preferably comprises at least 1.0 wt. % ALA based on total fatty acids. Preferably the composition comprises at least 1.5 wt. % ALA based on total fatty acids, more preferably at least 2.0 wt. %. Preferably the composition comprises less than 10 wt. % ALA, more preferably less than 5.0 wt. % based on total fatty acids. The weight ratio LA/ALA preferably is well balanced in order to improve BMD, while at the same time ensuring a normal growth and development. Therefore, the present composition preferably comprises a weight ratio of LA/ALA between 2 and 15, more preferably between 2 and 7, more preferably between 4 and 7, more preferably between 3 and 6, even more preferably between 4 and 5.5, even more preferably between 4 and 5.

Preferably the present composition comprises n-3 LC-PUFA, since n-3 LC-PUFA improve peak bone mass density. More preferably, the present composition comprises EPA, DPA and/or DHA, even more preferably DHA. Since a low concentration of DHA, DPA and/or EPA is already effective and normal growth and development are important, the content of n-3 LC-PUFA in the present composition, preferably does not exceed 15 wt. % of the total fatty acid content, preferably does not exceed 10 wt. %, even more preferably does not exceed 5 wt. %. Preferably the present composition comprises at least 0.2 wt. %, preferably at least 0.5 wt. %, more preferably at least 0.75 wt. %, n-3 LC-PUFA of the total fatty acid content.

As the group of n-6 fatty acids, especially arachidonic acid (AA) and LA as its precursor, counteracts the group of n-3 fatty acids, especially DHA and EPA and ALA as their precursor, the present composition comprises relatively low amounts of AA. The n-6 LC-PUFA content preferably does not exceed 5 wt. %, more preferably does not exceed 2.0 wt. %, more preferably does not exceed 0.75 wt. %, even more preferably does not exceed 0.5 wt. %, based on total fatty acids. Since AA is important in infants for optimal functional membranes, especially membranes of neurological tissues, the amount of n-6 LC-PUFA is preferably at least 0.02 wt. % more preferably at least 0.05 wt. %, more preferably at least 0.1 wt. % based on total fatty acids, more preferably at least 0.2 wt. %. The presence of AA is advantageous in a composition low in LA since it remedies LA deficiency. The presence of, preferably low amounts, of AA is beneficial in nutrition to be administered to infants below the age of 6 months, since for these infants the infant formulae is generally the only source of nutrition.

Preferably, in addition to the vegetable lipid, a lipid selected from fish oil (preferably tuna fish oil) and single cell oil (such as algal, microbial oil and fungal oil) is present. These sources of oil are suitable as LC-PUFA sources. Preferably as a source of n-3 LC-PUFA single cell oil, including algal oil and microbial oil, is used.

Process for Obtaining Phospholipid Coated Lipid Globules

The present composition comprises lipid globules. The lipid globule size can be manipulated by adjusting process steps by which the present composition is manufactured. A suitable and preferred way to obtain lipid globules coated with phospholipids is to increase the amount of phospholipids compared to amounts typically present in infant formula and to have these phospholipids present during the homogenization process, wherein the mixture of aqueous phase and oil phase is homogenized. Typical amounts of phospholipids/polar lipids in infant formula are about 0.15 wt. %/0.2 wt. % based on total fat. The amount of phospholipids is increased to at least 0.5 wt %, more preferably at least 1.0 wt. % based on total fat or the amount of phospholipids is increased to at least 0.6 wt. %, more preferably at least 1.0 wt. % based on total fat. In standard infant milk formula the lipid fraction (usually comprising vegetable fat, a small amount of phospholipids and fat soluble vitamins) is mixed into the aqueous fraction (usually comprising water, skimmed milk, whey, digestible carbohydrates such as lactose, water soluble vitamins and minerals and optionally non-digestible carbohydrates) by homogenization. If no homogenization was to take place, the lipid part would cream very quickly, i.e. separate from the aqueous part and collect at the top. Homogenization is the process of breaking up the fat phase into smaller sizes so that it no longer quickly separates from the aqueous phase but is maintained in a stable emulsion. This is accomplished by forcing the milk at high pressure through small orifices.

The process comprises the following steps:

1 Mixing Ingredients

The ingredients of the composition are mixed, e.g. preferably blended. Basically a lipid phase, comprising the vegetable lipids, and an aqueous phase are added together. The ingredients further comprise polar lipids, more preferably phospholipids. The ingredients of the aqueous phase may comprise water, skimmed milk (powder), whey (powder), low fat milk, lactose, water soluble vitamins and minerals. Preferably the aqueous phase comprises non-digestible oligosaccharides. Preferably the aqueous phase is set at a pH between 6.0 and 8.0, more preferably pH 6.5 to 7.5. Preferably the polar lipids, in particular the phospholipids, are derived from milk. Advantageously, having polar lipids present in the aqueous mixture before homogenization results in an efficient coating of the lipid globules, consisting essentially of triglycerides, with a coating of phospholipids.

Preferably the lipid phase comprises 50 to 100 wt. % vegetable lipids based on total weight of the lipid phase. Instead of in the aqueous phase, the phospholipids, more preferably the phospholipids, may also be present in the lipid phase or in both phases. Alternatively the phospholipids may be added separately to an aqueous and lipid phase. The weight ratio of phospholipid to total lipid is from 1.0 to 20 wt. %, more preferably from 1.0 to 10 wt. %, even more preferably 3 to 8 wt. %. Preferably the weight ratio of polar lipids tot total lipid is 1.0 to 25 wt. %, more preferably from 1.2 to 12 wt. %

The aqueous and lipid phase are preferably heated before adding together, preferably at a temperature of 40° C. to 80° C., more preferably 55° C. to 70° C., even more preferably 55° C. to 60° C. The mixture is also kept at this temperature and blended. A suitable way for blending is using an Ultra-Turrax T50 for about 30-60 s at 5000-10000 rpm. Subsequently demi-water may be added to this blend, to obtain the desired dry matter %. A desired dry matter % is for example 15%. Alternatively, the lipid phase is injected to the aqueous phase immediately prior to homogenization.

Minerals, vitamins, and stabilizing gums may be added at various points in the process depending on their sensitivity to heat. Mixing can for instance be performed with a high shear agitator. In the process of the present invention, skimmed milk (casein) is preferably not present in this step and added to the composition after homogenization of the fat fraction into the aqueous fraction (comprising compounds such as whey, whey protein, lactose).

2 Pasteurization

Preferably the mixture is then pasteurized. Pasteurization involves a quick heating step under controlled conditions which microorganisms cannot survive. A temperature of 60 to 80° C., more preferably 65 to 75° C., held for at least 15 s, usually adequately reduces vegetative cells of microorganisms. Several pasteurization methods are known and commercially feasible. Alternatively this step can also be performed before mixing as in step 1 and/or be replaced by the heating step to 60° C. in step 1.

3 Homogenization

Subsequently the optionally pasteurized mixture comprising vegetable lipids, phospholipids and an aqueous phase is homogenized. Homogenization is a process which increases emulsion uniformity and stability by reducing the size of the lipid globules in the formula. This process step can be performed with a variety of mixing equipment, which applies high shear to the product. This type of mixing breaks the lipid globules into smaller globules. The mixture obtained is preferably homogenized in two steps, for example at 250 to 50 bar, respectively, so a total pressure of 300 bar in order to obtain small, stable lipid globules.

In case the size of the lipid globules is preferred to be larger the homogenization steps are performed under much lower pressures. For example 60° C. at 5 to 100, preferably 30-100, bar and 5 to 50 bar respectively, with a total pressure of 35 to 150 bar. Alternatively, the mixture obtained is preferably homogenized in two steps at a lower temperature, between 15 and 40° C., preferably about 20° C. at 5 to 50 and 5 to 50 bar respectively, with a total pressure of 5 to 100 bar. This is remarkably lower than standard pressures, which typically are 250 to 50 bar, respectively, so a total pressure of 300 bar. It will be dependent on the specific homogenizer used, which pressure to apply. A suitable way is to use a pressure of 100 bar in the first step and 50 bar in the second step in a Niro Suavi NS 2006 H Homogenizer at a temperature of 60° C. A suitable way is to use a pressure of 5 bar in the first step and 20 bar in the second step in a Niro Suavi NS 2006 H Homogenizer at a temperature of 20° C.

Subsequently optionally other ingredients, not being lipid, may be added.

4 Sterilization

Subsequently, the emulsion obtained in step 3 is preferably sterilized. Preferably sterilization takes place in-line at ultra high temperature (UHT) and/or in appropriate containers to obtain a formula in the form of a sterile liquid. A suitable way for UHT treatment is a treatment at 120-130° C. for at least 20 s. Alternatively, this sterilization step 4 is performed before the homogenization step 3.

Preferably the composition obtained by the above process is spray dried afterwards.

Alternatively, the emulsion obtained in step 3 is concentrated by evaporation, subsequently sterilized at ultra high temperature and subsequently spray dried to give a spray dried powder which is filled into appropriate containers.

The difference on coating of the lipid globules can further be derived from the zeta potential. Zeta potential ($\zeta$ potential) measures the difference in milliVolts (mV) in electrokinetic potential between the tightly bound layer around the surface and the distant zone of electroneutrality and is a measure of the magnitude of the repulsion or attraction between particles in a dispersion. Its value is also related to the stability of colloidal dispersions. A high absolute zeta potential will confer stability, i.e. the solution or dispersion will resist aggregation.

Lipid Globule Size

According to the present invention, lipid is present in the composition in the form of lipid globules, emulsified in the aqueous phase. The lipid globules comprise a core and a coating. The core comprises vegetable fat and preferably comprises at least 90 wt. % triglycerides and more preferably essentially consists of triglycerides. The coating comprises phospholipids and optionally other polar lipids. Not all phospholipids and/or polar lipids that are present in the composition need necessarily be comprised in the coating, but preferably a major part is. Preferably more than 50 wt. %, more preferably more than 70 wt,%, even more preferably more than 85 wt. %, most preferably more than 95 wt. % of the phospholipids and/or polar lipids that are present in the composition are comprised in the coating of lipid globules. Not all vegetable lipids that are present in the composition need necessarily be comprised in the core of lipid globules, but preferably a major part is, preferably more than 50% wt. %, more preferably more than 70 wt. %, even more preferably more than 85 wt. %, even more preferably more than 95 wt. %, most preferably more than 98 wt. % of the vegetable lipids that are present in the composition are comprised in the core of lipid globules.

In one embodiment the lipid globules of the present invention preferably have
1. a volume-weighted mode diameter above 1.0 μm, preferably above 3.0 μm, more preferably 4.0 μm or above, preferably between 1.0 and 10 μm, more preferably between 2.0 and 8.0 μm, even more preferably between 3.0 and 8.0 μm, most preferably between 4.0 μm and 8.0 μm and/or
2. a size distribution in such a way that at least 45 volume %, preferably at least 55 volume %, even more preferably at least 65 volume %, even more preferably at least 75 volume % has a diameter between 2 and 12 μm. More preferably at least 45 volume %, preferably at least 55 volume %, even more preferably at least 65 volume %, even more preferably at least 75 volume % has a diameter between 2 and 10 μm. Even more preferably at least 45 volume %, preferably at least 55 volume %, even more preferably at least 65 volume %, even more preferably at least 75 volume % has a diameter between 4 and 10 μm.

In another preferred embodiment the lipid globules of the present invention preferably have
1. a volume-weighted mode diameter below 1.0 μm, and preferably in the range of 0.2-0.7 μm, more preferably in the range of 0.3-0.6 μm, and
2. a size distribution in such a way that less than 45 volume %, has a diameter between 2 and 12 μm, preferably a size distribution wherein more than 55 volume % of the lipid globules has a diameter of less than 2 μm, more preferably a size distribution in such a way that less than 35 volume %, has a diameter between 2 and 12 μm, even more preferably a size distribution wherein more than 65 volume % of the lipid globules has a diameter of less than 2 μm.

The percentage of lipid globules is based on volume of total lipid. The mode diameter relates to the diameter which is the most present based on volume of total lipid, or the peak value in a graphic representation, having on the X-as the diameter and on the Y-as the volume (%).

The volume of the lipid globule and its size distribution can suitably be determined using a particle size analyzer such as a Mastersizer (Malvern Instruments, Malvern, UK), for example by the method described in Michalski et al, 2001, Lait 81: 787-796.

Digestible Carbohydrate Component

The composition preferably comprises digestible carbohydrate. The digestible carbohydrate preferably provides 30 to 80% of the total calories of the composition. Preferably the digestible carbohydrate provides 40 to 60% of the total calories. When in liquid form, e.g. as a ready-to-feed liquid, the composition preferably comprises 3.0 to 30 g digestible carbohydrate per 100 ml, more preferably 6.0 to 20, even more preferably 7.0 to 10.0 g per 100 ml. Based on dry weight the present composition preferably comprises 20 to 80 wt. %, more preferably 40 to 65 wt. % digestible carbohydrates.

Preferred digestible carbohydrate sources are lactose, glucose, sucrose, fructose, galactose, maltose, starch and maltodextrin. Lactose is the main digestible carbohydrate present in human milk. The present composition preferably comprises lactose. The present composition preferably comprises digestible carbohydrate, wherein at least 35 wt. %, more preferably at least 50 wt. %, more preferably at least 75 wt. %, even more preferably at least 90 wt. %, most preferably at least 95 wt. % of the digestible carbohydrate is lactose. Based on dry weight the present composition preferably comprises at least 25 wt. % lactose, preferably at least 40 wt. %.

Non-Digestible Oligosaccharides

Preferably the present composition comprises non-digestible oligosaccharides with a degree of polymerization (DP) between 2 and 250, more preferably 3 and 60. The non-digestible oligosaccharides advantageously improve mineral absorption, bone composition and architecture. The underlying mechanisms are via an increased solubility of minerals is presumed to be via an increased bacterial production of short-chain fatty acids in the intestine, and/or an enlargement of the intestinal absorption surface by promoting proliferation of enterocytes mediated by these short chain fatty acids. Therefore the non-digestible oligosaccharides are presumed to enhance the BMD and/or BMC increasing effects of the coated lipid globules of the composition according to the present invention.

The non-digestible oligosaccharide is preferably selected from the group consisting of fructo-oligosaccharides (such as inulin), galacto-oligosaccharides (such as transgalacto-oligosaccharides or beta-galacto-oligisaccharides), gluco-oligosaccharides (such as gentio-, nigero- and cyclodextrin-oligosaccharides), arabino-oligosaccharides, mannan-oligosaccharides, xylo-oligosaccharides, fuco-oligosaccharides, arabinogalacto-oligosaccharides, glucomanno-oligosaccharides, galactomanno-oligosaccharides, sialic acid comprising oligosaccharides and uronic acid oligosaccharides. Preferably the composition comprises gum acacia on combination with a non-digestible oligosaccharide.

Preferably the present composition comprises fructo-oligosaccharides, galacto-oligosaccharides and/or galacturonic acid oligosaccharides, more preferably galacto-oligosaccharides, most preferably transgalacto-oligosaccharides. In a preferred embodiment the composition comprises a mixture of transgalacto-oligosaccharides and fructo-oligosaccharides. Preferably the present composition comprises galacto-oligosaccharides with a DP of 2-10 and/or fructo-oligosaccharides with a DP of 2-60. The galacto-oligosaccharide is preferably selected from the group consisting of transgalacto-oligosaccharides, lacto-N-tetraose (LNT), lacto-N-neotetraose (neo-LNT), fucosyl-lactose, fucosylated LNT and fucosylated neo-LNT. In a particularly preferred embodiment the present method comprises the administration of transgalacto-oligosaccharides([galactose]$_n$-glucose; wherein n is an integer between 1 and 60, i.e. 2, 3, 4, 5, 6, . . . , 59, 60; preferably n is selected from 2, 3, 4, 5, 6, 7, 8, 9, or 10). Transgalacto-oligosaccharides (TOS) are for example sold under the trademark Vivinal™ (Borculo Domo Ingredients, Netherlands). Preferably the saccharides of the transgalacto-oligosaccharides are β-linked.

Fructo-oligosaccharide is a non-digestible oligosaccharide comprising a chain of β linked fructose units with a DP or average DP of 2 to 250, more preferably 10 to 100. Fructo-oligosaccharide includes inulin, levan and/or a mixed type of polyfructan. An especially preferred fructo-oligosaccharide is inulin. Fructo-oligosaccharide suitable for use in the compositions is also already commercially available, e.g. Raftiline®HP (Orafti).

Uronic acid oligosaccharides are preferably obtained from pectin degradation. Uronic acid oligosaccharides are preferably galacturonic acid oligosaccharides. Hence the present composition preferably comprises a pectin degradation product with a DP between 2 and 100. Preferably the pectin degradation product is prepared from apple pectin, beet pectin and/or citrus pectin. Preferably the composition comprises transgalacto-oligosaccharide, fructo-oligosaccharide and a pectin degradation product. The weight ratio transgalacto-oligosaccharide:fructo-oligosaccharide:pectin degradation product is preferably (20 to 2):1:(1 to 3), more preferably (12 to 7):1:(1 to 2).

Preferably, the composition comprises of 80 mg to 2 g non-digestible oligosaccharides per 100 ml, more preferably 150 mg to 1.50 g, even more preferably 300 mg to 1 g per 100 ml. Based on dry weight, the composition preferably comprises 0.25 wt. % to 20 wt. %, more preferably 0.5 wt. % to 10 wt. %, even more preferably 1.5 wt. % to 7.5 wt. %. A lower amount of non-digestible oligosaccharides will be less effective in effect on BMC and/or BMD, whereas a too high amount will result in side-effects of bloating and abdominal discomfort.

Protein Component

The present composition preferably comprises proteins. The protein component preferably provides 5 to 15% of the total calories. Preferably the present composition comprises a protein component that provides 6 to 12% of the total calories. More preferably protein is present in the composition below 9% based on calories, more preferably the composition comprises between 7.2 and 8.0% protein based on total calories, even more preferably between 7.3 and 7.7% based on total calories. A low protein concentration advantageously ensures a lower insulin response, thereby preventing proliferation of adipocytes in infants. Human milk comprises a lower amount of protein based on total calories than cow's milk. The protein concentration in a nutritional composition is determined by the sum of protein, peptides and free amino acids. Based on dry weight the composition preferably comprises less than 12 wt. % protein, more preferably between 9.6 to 12 wt. %, even more preferably 10 to 11 wt. %. Based on a ready-to-drink liquid product the composition preferably comprises less than 1.5 g protein per 100 ml, more preferably between 1.2 and 1.5 g, even more preferably between 1.25 and 1.35 g.

The source of the protein should be selected in such a way that the minimum requirements for essential amino acid content are met and satisfactory growth is ensured. Hence protein sources based on cows' milk proteins such as whey, casein and mixtures thereof and proteins based on soy, potato or pea are preferred. In case whey proteins are used, the protein source is preferably based on acid whey or sweet whey, whey protein isolate or mixtures thereof and may include α-lactalbumin and β-lactoglobulin. More preferably, the protein source is based on acid whey or sweet whey from which caseino-glyco-macropeptide (CGMP) has been removed. Removal of CGMP from sweet whey protein advantageously reduces the threonine content of the sweet whey protein. A reduced threonine content is also advantageously achieved by using acid whey. Optionally the protein source may be supplemented with free amino acids, such as methionine, histidine, tyrosine, arginine and/or tryptophan in order to improve the amino acid profile. Preferably α-lactalbumin enriched whey protein is used in order to optimize the amino acid profile. Using protein sources with an optimized amino acid profile closer to that of human breast milk enables all essential amino acids to be provided at reduced protein concentration, below 9% based on calories, preferably between 7.2 and 8.0% based on calories and still ensure a satisfactory growth. If sweet whey from which CGMP has been removed is used as the protein source, it is preferably supplemented by free arginine in an amount of from 0.1 to 3 wt. % and/or free histidine in an amount of from 0.1 to 1.5 wt. % based on total protein.

Casein is advantageously present. During digestion of casein casein phosphopeptide (CPP) is released which improves BMD and/or BMC. CPP improves calcium absorption in the small intestine. Preferably the composition comprises at least 3 wt. % casein based on dry weight. Preferably the casein is intact and/or non-hydrolyzed.

Preferably the composition comprises calcium. Calcium is the major cation of bone mineral. Preferably the composition comprises at least 200 mg calcium based on 100 g dry weight, more preferably at least 300 mg, even more preferably at least 350 mg/100 g dry weight. Preferably the composition comprises less than 1500 mg calcium per 100 g dry weight, more preferably less than 1000 mg even more preferably less than 800 mg/100 g dry weight.

Preferably the composition comprises phosphate. Phosphate is the major anion of bone mineral. Preferably the composition comprises at least 100 mg phosphate based on 100 g dry weight, more preferably at least 150 mg, even more preferably at least 200 mg/100 g dry weight. Preferably the composition comprises less than 1000 mg phosphate per 100 g dry weight, more preferably less than 500 mg even more preferably less than 350 mg/100 g dry weight.

Preferably the weight ratio calcium to phosphate is between 2.5 and 1.0, more preferably between 2.0 and 1.5. A balanced calcium phosphate ratio beneficially effects BMD and/or BMC in infants.

Preferably the composition comprises vitamin D. Vitamin D regulates the calcium and phosphorus levels in the blood by promoting their absorption from food in the intestines, and by promoting re-absorption of calcium in the kidneys, which enables normal mineralization of bones. It is also needed for bone growth and bone remodeling by osteoblasts and osteoclasts. Preferably the composition comprises at least 3 μg vitamin D based on 100 g dry weight, more preferably at least 5 μg, even more preferably at least 8 μg/100 g dry weight. Preferably the composition comprises less than 100 μg vitamin D per 100 g dry weight, more preferably less than 50 μg, even more preferably less than 20 μg/100 g dry weight.

Nutritional Composition

The present composition is preferably particularly suitable for providing the daily nutritional requirements to a human with an age below 36 months, particularly an infant with the age below 24 months, even more preferably an infant with the age below 18 months, most preferably below 12 months of age. Hence, the nutritional composition is for feeding or is used for feeding a human subject. The present composition comprises a lipid, and preferably a protein and preferably a digestible carbohydrate component wherein the lipid component preferably provides 30 to 60% of total calories, the protein component preferably provides 5 to 20%, more preferably 5 to 15 wt. %, of the total calories and the digestible carbohydrate component preferably provides 25 to 75% of the total calories. Preferably the present composition comprises a lipid component providing 35 to 50% of the total calories, a protein component provides 6 to 12% of the total calories and a digestible carbohydrate component provides 40 to 60% of the total calories. The amount of total calories is determined by the sum of calories derived from protein, lipids and digestible carbohydrates.

The present composition is not human breast milk. The present composition comprises vegetable lipids. The compositions of the invention preferably comprise other fractions, such as vitamins, minerals according to international directives for infant formulae.

In one embodiment the composition is a powder suitable for making a liquid composition after reconstitution with an aqueous solution, preferably with water. Preferably the composition is a powder to be reconstituted with water. It was surprisingly found that the size and the coating with phospholipids of the lipid globules remained the same after the drying step and subsequent reconstitution.

In order to meet the caloric requirements of the infant, the composition preferably comprises 50 to 200 kcal/100 ml liquid, more preferably 60 to 90 kcal/100 ml liquid, even more preferably 60 to 75 kcal/100 ml liquid. This caloric density ensures an optimal ratio between water and calorie consumption. The osmolarity of the present composition is preferably between 150 and 420 mOsmol/l, more preferably 260 to 320 mOsmol/l. The low osmolarity aims to reduce the gastrointestinal stress. Stress can induce adipocyte formation.

Preferably the composition is in a liquid form, with a viscosity below 35 mPa·s, more preferably below 6 mPa·s as measured in a Brookfield viscometer at 20° C. at a shear rate of 100 $s^{-1}$. Suitably, the composition is in a powdered from, which can be reconstituted with water to form a liquid, or in a liquid concentrate form, which should be diluted with water. When the composition is in a liquid form, the preferred volume administered on a daily basis is in the range of about 80 to 2500 ml, more preferably about 450 to 1000 ml per day.

Infant

Bone growth is very fast during infancy. Hence, the present composition is therefore advantageously administered to a human of 0-36 months, more preferably to a human of 0-18 months, more preferably to a human of 0-12 months, even more preferably to a human of 0-6 months.

Preferably the composition is to be used in infants which are prematurely born or which are small for gestational age. These infants experience after birth a catch up growth, which is an extra risk for developing a too low BMD and/or BMC later in life.

Application

In one embodiment, the present method further is for preventing obesity, or in other words, the nutritional composition is further for prevention of obesity or the nutritional composition is for further use in prevention of obesity.

The present composition is preferably administered orally to the infant. According to the present invention the BMD and/or BMC increase, particularly at the age above 5 years, particularly above 13 years, more particularly above 18 years.

The inventors surprisingly found that when mice were fed, during infancy and childhood, a food composition comprising lipid globules coated with phospholipids, a different and significant effect on body composition later in life was observed compared to mice which during infancy and childhood had been fed a food composition having a similar fatty acid composition, but not a coating with phospholipids. At day 42, a day corresponding to childhood in a human setting, no difference was observed in growth (weight) between the two groups, but from day 42 both groups were fed a Western style diet which was high in fat and high in palmitic acid. Surprisingly at day 70, 98 and 126, which are a time points corresponding to early adulthood and adulthood respectively in humans, the mice, which had previously consumed the food composition of the present invention before turning to the Western style diet, had a significantly increased bone mineral content and increased bone mass density than mice which had received a control composition during infancy. The effects were even more pronounced when the lipid globules were increased in size.

This indicates that early nutrition has an effect on BMD and/or BMC extending beyond the period in which it is actually administered. In one embodiment the effect on BBM and/or BMC occurs later in life. With later in life is meant an age exceeding the age at which the diet is taken, preferably with at least one year.

The important difference between the two formulae was the coating of the lipid globules with phospholipids. The fatty acid profile was similar in both formulae and the amount of palmitic and stearic acid present at sn-1 and sn-3 positions in the fat was also similar. Both formulae further enabled a similar good growth and development early in life. The present inventors believe that the difference in lipid globule architecture, in particularly the coating by phospholipids, between the composition of the present invention and conventional infant formulae on bone health cannot be explained by an effect on improved calcium absorption via a decrease of palmitic and/or stearic acid calcium soap formation as known from the prior art with structured lipids. Furthermore, the use of such lipids exerted a different effect on body composition, such as body weight, lean body mass and fat mass, as shown in example 4.

The present invention therefore can be used for food compositions intended for infants and/or toddlers in order to increase bone mineral content and/or increase bone mass density. The present invention therefore can be used for food compositions intended for infants and/or toddlers in order to prevent or reduce the risk for osteoporosis later in life, for the enhancement of bone formation and bone mass maximization and for the enhancement of bone formation in infants and young children. Also qualifications like 'enhances bone strength' or 'for stronger bones' and the like are encompassed by the use or method according to the present invention.

The present invention also allows to formulate infant milk formulae with high levels of palmitic and stearic acid, as observed in human milk and with the use of natural lipids, i.e. without the use of synthetically made triglycerides, which are more expensive and subject to strict food legislations In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

EXAMPLES

Example 1

Process for Preparing an IMF with Polar Lipid Coated Lipid Globules

Example 1A

Infant formulae were prepared by dissolving using demineralised whey powder, lactose, whey protein concentrate, skim milk powder, galacto-oligosaccharides, minerals and vitamin pre-mix in demineralised water to a dry weight content of 22.5 g/100 g and heating the water phase at 65° C.

The oil blend was prepared using over 98 wt. % vegetable oils, an oil comprising LC-PUFA, oil soluble vitamins and antioxidants. Both the water phase and the oil blend were heated to 65° C. prior to mixing. The oil blend was added to the water phase and blended with an Ultra-Turrax T50 for about 30-60 s at 5000-1000 rpm. The dry weight of this mixture was about 26%. The product was UHT treated for 30 s at 125° C. and subsequently cooled to 20° C.

The homogenization pressure was 200 and 50 bar, respectively in a Niro Suavi NS 2006 H homogenizer. The products were dried to a powder by spray drying. Long chain inulin was blended dry into the powder. For diet 1 no added polar lipids were present. The amount of vegetable glycerophospholipids was 0.2 wt. % based on total fat for diet 1. Diet 1 did not contain sphingolipids and cholesterol. For diet 2, and 3 a butter milk powder was used. Diet 2 and 3 comprised 1.83 wt. % glycerophospholipids based on total fat, of which about 90% derived from the butter milk powder and about 10% already present in the standard IMF derived from vegetable oils, and further comprised milk derived sphingolipids of which the majority (about 0.47 wt. % based on total fat) was sphingomyelin; the rest being glycosphingolipids, of which the majority (over 60%) is GD3 with a concentration of about 0.13 wt. % based on total fat. Diet 2 and 3 comprised about 0.05 wt. % milk derived cholesterol based on total fat.

In diet 2 the butter milk powder comprising these polar lipids were dry blended after the homogenization, sterilization and spray dry step in order to prevent coating of the lipid globules. In diet 3 the butter milk polar lipids were present in the aqueous phase during the homogenization step in order to coat the lipid globules.

The size of the lipid globules was measured with a Mastersizer 20000 (Malvern Instruments, Malvern UK) and shown in Table 1. It was checked with confocal laser scanning microscopy that the lipid globules were coated or not with phospholipids, before spray drying. As fluorescent probes Annexin V Alexa Fluor 488 (In Vitrogen molecular probes) for labeling phospholipids, and Nile Red (Sigma-Aldrich) for labeling triglycerides, were used. After labeling the milk samples Vectrahield mounting medium (Vector laboratories inc. Burliname USA) for reducing particle movement and photo-bleaching was added. Observations were made using a Zeiss Laser Scanning Microscope with excitation wavelengths of 488/543/633 nm and emission filters set at band pass 505-530, and band pass 560-615. No coating with phospholipids was observed with IMF 1 and 2, but coating with phospholipids was observed with IMF 3.

TABLE 1

Lipid globule characteristics of different milks

| IMF | Coating | Volume Mode diameter μm | Volume % with a diameter between 2 and 12 μm |
|---|---|---|---|
| 1, Standard IMF | − | 0.5 | 5.1 |
| 2, Experimental IMF (free polar lipids) | − | 0.4 | 3.9 |
| 3, Experimental IMF of present invention (lipid globules coated with phospholipids) | + | 0.5 | 4.3 |

The size of the lipid globules was measured with a Mastersizer 20000 (Malvern Instruments, Malvern UK) and shown in Table 1.

After 5 months storage at room temperature the size of the lipid globules in diet 1, 2 and 3 had not changed.

Example 1B

An infant formula was prepared comprising per kg powder 4800 kcal, 248 g lipid, 540 g digestible carbohydrates, 55 g non-digestible oligosaccharides and 103 g protein. The composition was prepared using BAEF powder (Corman, Goé, Belgium), a vegetable oil blend, demineralised whey powder, lactose, non-digestible oligosaccharides (galacto-oligosaccharides and long chain fructo-oligosaccharides in a weight ratio of 9/1). Also vitamins, minerals, trace elements as known in the art were used.

The amount of BAEF was such that 7.24 wt. % phospholipids (from BAEF) based on total lipids were present in the composition. Based on a small amounts of phospholipids in the oil blend, the total amount of phospholipids was 7.39 wt. % based on total lipid. BAEF also supplied a small amount of cholesterol (about 0.08 wt. % based on total lipid of the infant formula) and glycosphingolipids (about 1.65% glycosphingolipids based on total lipid of the infant formula).

The BAEF powder was mixed with galacto-oligosaccharides, lactose, vitamin pre-mixtures and mineral premixes in water, at room temperature, by stiffing. Potassium hydroxide was used to set the pH at 6.8-7.0. The dry weight matter of the mixture was about 27%. The mixture was heated to 60° C. The vegetable oil blend was also heated to 60° C. and added to the water phase and blended with an Ultra-Turrax T50 for about 30-60 s at 5000-10000 rpm. Subsequently demi-water was added to achieve a dry matter content of about 15%.

Subsequently the oil-water mixture was homogenised at a pressure of 100 bar in a first step and 50 bar in a second step in a Niro Suavi NS 2006 H Homogenizer. The temperature was 60° C. Subsequently demineralized whey powder was added to arrive at a final dry matter content of 18%. The product was UHT treated at 125° C. for 30 s. The product was dried to a powder by spray drying. Maltodextrin together with long chain inulin was blended dry into the powder.

The size of the lipid globules was measured with a Mastersizer 20000 (Malvern Instruments, Malvern UK). The volumetric mode diameter was 7.3 µm. A second, much smaller peak was present at 0.52 µm. The volume % of lipid globules with a size between 2 and 12 m was 71% based on total lipid volume. It was checked with confocal laser scanning microscopy that the larger lipid globules of the present invention were coated with phospholipids, before spray drying and after reconstitution of the spray dried powder with water. In both cases the lipid globules were covered with a layer of phospholipids. As fluorescent probes Annexin V Alexa Fluor 488 (In Vitrogen molecular probes) for labeling the phospholipids, and Nile Red (Sigma-Aldrich) for labeling triglycerides, were used. After labeling the milk samples Vectrahield mounting medium (Vector laboratories inc., Burliname USA) for reducing particle movement and photobleaching was added. Observations were made using a Zeiss Laser Scanning Microscope with excitation wavelengths of 488/543/633 nm and emission filters set at band pass 505-530, and band pass 560-615. Also the size of the lipid globules was the same before drying and after reconstitution of the spray dried powder with water.

As a control the lipid globules of a standard infant formula (Nutrilon 1) did not show labeling with phospholipids as observed with the confocal laser scanning microscopy. Instead the globules were covered with protein, as determined with the fluorescent protein stain Fast Green FCF. The volumetric modal diameter of the lipid globules in this standard infant milk formula was measured to be 0.5 µm. A second much smaller peak was present at 8.1 µm. The volume % of lipid globules with a size between 2 and 12 m was 34% based on total lipid volume.

Also human milk was analyzed and showed a volumetric modal diameter of the lipid globules of 5.3 µm. The volume % of lipid globules with a size between 2 and 12 m was 98% based on total lipid volume. The lipid globules were covered with a layer of phospholipids. The zeta potentials and volume weighted mean diameters were also measured. The results are shown in table 2.

TABLE 2

Lipid globule characteristics of different milks

| | Volume Mode diameter µm | Volume % with a diameter between 2 and 12 µm | ζ potential (mV) |
|---|---|---|---|
| Standard infant milk formula (Nutrilon 1) | 0.5 | 34 | −22.4 |
| Infant milk formula of the invention | 7.3 | 71 | −16 |
| Human milk | 5.3 | 98 | −13.8 |

Example 2

Programming Effect of Lipid Globule Size on Adult Body Composition

Offspring of C57/BL6 dams were weaned from day 15 on. The experimental weaning diets were continued until day 42. From day 42 to day 98 all pups were fed the same diet based on AIN-93G diet with an adjusted lipid fraction (containing 10 wt. % lipid of which 50 wt. % lard and 1% cholesterol, based on total lipid), which is representative for a Western style diet.

The experimental diets that were used for weaning were:

1) an infant milk formula (IMF) based control diet. This diet comprised 282 g standard IMF per kg, IMF 1 of example 1A, i.e. small lipid globules. The rest of the diet was AIN-93G protein, carbohydrates and fibre. All lipid present in the diet was derived from the IMF.

2) an IMF based control diet. This diet differed from diet 1 in that it comprised 282 g IMF 2 of example 1A, i.e. comprised phospholipids, additionally added to the dry mixture.

3) a diet based on the IMF of the present invention. This diet differed from diet 1 and 2 that it comprises 282 g IMF3 of example 1A i.e. with lipid globules coated phospholipids. All lipid present in the diet was derived from the IMF.

At day 42, all mice switched to a "Western style diet" comprising 10 wt. % lipid until day 98. The fatty acid composition of the two experimental was the same with calculated linoleic acid (LA) of 14% based on total fatty acids, with alpha linolenic acid (ALA) of 2.6 in based on total fatty acids and with LA/ALA of 5.4. The amount of DHA was 0.2 wt. % and the amount of ARA was 0.35 wt. %. The fatty acid composition of the Western style diet shown in table 5.

The mice were weighed twice a week. The food intake was determined once a week during the entire experiment. To determine body composition (i.e., BMC, BMD, fat mass (FM) and fat-free mass (FFM)) DEXA scans (Dual Energy X-ray Absorbiometry) were performed under general anesthesia at 6, 10 and 14 weeks of age, 42, 70, and 98 days after birth respectively, by densitometry using a PIXImus imager (GE Lunar, Madison, Wis., USA). At the age of 98 days the male mice were sacrificed.

Results:

No effect on growth (body weight) and food intake was observed during the experimental period between the groups. Moreover, the development of body weight and fat mass (determined with DEXA) was not significantly different at day 42 (end of the diet intervention period). The BMD and BMC were lower in the mice receiving diet 3 than in the mice receiving diet 1. A subsequent treatment with a Western style diet between day 42 and day 98 of all groups resulted in clear differences in body composition at the end of the experiment (day 98), see Table 3. There was no difference in effects on BMD at day 98. However, the increase in BMD between day 42 and 98 was significantly higher in the mice receiving IMF 3 than the mice receiving the control diet 1. This was due to the coating since the increase observed with diet 2 was not significant compared to diet 1. On day 98 the BMC was higher in mice receiving the lipid with coated lipid globules (diet 3 versus diet 1). The increase in BMC between day 42 and 98 was significantly higher in mice receiving diet 3 than mice receiving diet 1. For diet 2 this increase in BMC was not observed. This is indicative that the effects on BMD and BMC are observed later in life when receiving a diet with phospholipid coated lipid globules early in life. Interestingly, the fat mass and relative fat mass developed later in life was reduced in the mice which had received the diet with the coated lipid globules during their infancy and childhood, compared to mice which had received the control diet or the diet wherein the lipids were not present in the coating.

TABLE 3

Bone Mineral Content, Bone Mass Density, Fat Mass and relative Fat Mass.

| Parameter | Day | Diet 1 | Diet 2 | Diet 3 |
|---|---|---|---|---|
| Body weight g (s.e.) | 42 | 25.84 (046) | 25.64 (0.59) | 24.50 (0.26) |
| | 70 | 30.93 (0.69) | 28.89 (0.80) | 30.19 (0.61) |
| | 98 | 33.98 (0.99) | 33.14 (0.82) | 32.08 (0.76) |
| Lean Body mass g (s.e.) | 42 | 20.83 (0.30) | 19.60 (0.58) | 19.39 (0.31) |
| | 70 | 20.34 (0.37) | 22.25 (0.40) | 21.41 (0.42) |
| | 98 | 22.89 (0.43) | 22.01 (0.51) | 22.20 (0.64) |
| Bone mineral content g Mean (s.e.) | 42 | 0.461 (0.009) | 0.431 (0.013) | 0.418 (0.009)* |
| | 70 | 0.475 (0.007) | 0.515 (0.014) | 0.492 (0.008) |
| | 98 | 0.538 (0.009) | 0.521 (0.10) | 0.555 (0.014) |
| Bone Mass Density g/cm$^2$ Mean (s.e.) | 42 | 0.049 (0.001) | 0.047 (0.001) | 0.046 (0.001)* |
| | 70 | 0.054 (0.001) | 0.054 (0.001) | 0.053 (0.001) |
| | 98 | 0.057 (0.001) | 0.057 (0.001) | 0.057 (0.001) |
| Fat mass g Mean (s.e.) | 42 | 4.42 (0.19) | 4.03 (0.19) | 3.74 (0.09) |
| | 70 | 5.94 (0.39) | 5.98 (0.53) | 5.83 (0.26) |
| | 98 | 8.35 (0.67) | 7.32 (0.52) | 6.95 (0.50) |
| Fat % of body weight Mean (s.e.) | 42 | 17.43 (0.49 | 17.03 (0.56) | 16.13 (0.36) |
| | 70 | 22.40 (0.99 | 20.78 (1.20) | 21.38 (0.96) |
| | 98 | 26.31 (1.33) | 24.63 (1.10) | 23.70 (1.25) |

It is concluded that food comprising lipid globules with an altered lipid architecture program and/or imprint the body early in life in such a way that later at life a healthier body composition has developed, with increased BMD and/or BMC, which prevents and/or reduces the risk for osteoporosis.

Example 3

Programming Effect of Lipid Globule Size on Adult Body Composition

The same experimental animal model and set up was used as in example 2, except that the experiment was terminated at day 126.

The experimental diets that were used for weaning were:

1) an infant milk formula (IMF) based control diet. This diet comprised 282 g standard IMF (Nutrilon 1) per kg, with the lipid globule size as mentioned in example 1B. The rest of the diet was AIN-93G protein, carbohydrates and fibre. All lipid present in the diet was derived from the IMF.

2) an IMF based diet of the present invention. This diet differed from diet 1 in that it comprised 282 g IMF of the invention of example 1B, i.e. comprised large lipid globules coated with phospholipids. All lipid present in the diet was derived from the IMF.

At day 42, all mice switched to a "Western style diet" comprising 10 wt. % lipid until day 126. The composition of the diets is given in table 3. The fatty acid composition of the two experimental and cafeteria diet is shown in table 4. The fatty acid profile of the two experimental diets was very similar.

TABLE 4 composition of experimental diets per kg

| | Diet 1, Control IMF | Diet 2, IMF of the invention | Western style diet |
|---|---|---|---|
| Kcal | 3922 | 3922 | 4016 |
| Lipid (g) | 70 | 70 | 100 |
| Phospholipids (g) | 0.12 | 5.16 | n.d. |
| Cholesterol (g) | 0.00 | 0.06 | 1 |
| Digestible Carbohydrates (g) | 644 | 644 | 600 |
| Lactose (g) | 145.9 | 145.9 | 0 |

TABLE 4-continued composition of experimental diets per kg

| | Diet 1, Control IMF | Diet 2, IMF of the invention | Western style diet |
|---|---|---|---|
| Sucrose, glucose (g) | 85 | 85 | 150 |
| Maltodextrin (g) | 360 | 360 | 450 |
| Fiber (g) | 47.5 | 47.5 | 47.5 |
| Protein | 179 | 179 | 179 | n.d. = not determined

The mice were weighed twice a week. The food intake was determined once a week during the entire experiment. To determine body composition (fat mass, fat free mass, bone mineral content and bone mass density) DEXA scans (Dual Energy X-ray Absorbiometry) were performed under general anesthesia at 6, 10 and 14 weeks of age, 42, 70, 98 and 126 days after birth respectively, by densitometry using a PIXImus imager (GE Lunar, Madison, Wis., USA). At the age of 126 days the male mice were sacrificed.

TABLE 5

Fatty acid composition of the experimental diets

| | Diet 1, Control IMF | Diet 2, IMF of the invention | Western style diet |
|---|---|---|---|
| C12:0 | 9.4 | 8.7 | 5.3 |
| C14:0 | 4.4 | 5.3 | 2.7 |
| C16:0 | 18.7 | 21.3 | 23.1 |
| C18:0 | 3.5 | 5.2 | 9.0 |
| C18:1 n-9 | 39.9 | 37.7 | 40.5 |
| C18:2 n-6 (LA) | 15.7 | 12.6 | 11.9 |
| C18:3 n-3 (ALA) | 2.4 | 2.1 | 1.3 |
| Others | 6.0 | 7.1 | 6.7 |
| n-6 | 16.0 | 12.9 | 11.9 |
| n-3 | 2.4 | 2.1 | 1.3 |
| n-6/n-3 | 6.58 | 6.12 | 9.1 |
| LA/ALA | 6.46 | 6.00 | 9.15 |
| SFA | 39.3 | 44.4 | 41.9 |
| MFA | 42.1 | 39.8 | 42.3 |
| PUFA | 18.3 | 14.9 | 13.2 |

Results:

No effect on growth (body weight) and food intake was observed during the experimental period between the groups. Moreover, the development of fat mass (determined with DEXA) was not significantly different at day 42 (end of the diet intervention period). The BMD was higher in the experimental group at day 42.

TABLE 6

Body weight, lean body mass, bone mineral content and bone mass density in time in mice receiving control or experimental diet during infancy

| Parameter | Day | Diet 1, Control IMF | Diet 2, IMF of the invention |
|---|---|---|---|
| Bodyweight g Mean (s.e.) | 42 | 23.50 (0.45) | 24.24 (0.51) |
| | 70 | 29.88 (0.46) | 30.16 (0.77) |
| | 98 | 33.32 (0.57) | 33.69 (0.95) |
| | 126 | 34.47 (0.80) | 34.15 (1.16) |
| Lean body mass g Mean (s.e.) | 42 | 18.96 (0.34) | 19.96 (0.40)* |
| | 70 | 21.31 (0.42) | 22.32 (0.48) |
| | 98 | 22.22 (0.49) | 23.91 (0.45)* |
| | 126 | 23.30 (0.43) | 24.19 (0.53)* |
| Bone Mineral Content g Mean (s.e.) | 42 | 0.364 (0.005) | 0.383 (0.009) |
| | 70 | 0.436 (0.007) | 0.474 (0.013)* |
| | 98 | 0.468 (0.011) | 0.501 (0.013)* |
| | 126 | 0.482 (0.000) | 0.523 (0.012)* |

TABLE 6-continued

Body weight, lean body mass, bone mineral content and bone mass density in time in mice receiving control or experimental diet during infancy

| Parameter | Day | Diet 1, Control IMF | Diet 2, IMF of the invention |
|---|---|---|---|
| Bone Mass Density g/cm² | 42 | 0.046 (0.000) | 0.048 (0.001)* |
| Mean (s.e.) | 70 | 0.051 (0.001) | 0.053 (0.001) |
|  | 98 | 0.052 (0.001) | 0.055 (0.001) |
|  | 126 | 0.052 (0.001)) | 0.055 (0.001) |
| Fat mass g | 42 | 3.78 (0.13) | 3.77 (0.21) |
| Mean (s.e.) | 70 | 7.84 (0.35) | 7.13 (0.65) |
|  | 98 | 10.68 (0.53) | 9.19 (0.79)* |
|  | 126 | 10.48 (0.67) | 9.11 (0.90)* |
| Fat % of body weight | 42 | 16.59 (0.45) | 15.83 (0.68) |
| Mean (s.e.) | 70 | 26.89 (1.07) | 23.81 (1.61) |
|  | 98 | 32.38 (1.42) | 27.25 (1.67)* |
|  | 126 | 30.78 (1.42) | 26.67 (1.77)* |

*$P < 0.05$ compared to control group

A subsequent treatment with a Western style diet between day 42 and day 126 of all groups resulted in clear differences in body composition at the end of the experiment (day 126), see Table 6. Both the BMC and BMD developed later in life were increased in the mice which had received the diet with the phospholipid coated, larger lipid globules during their infancy and childhood, compared to mice which had received the control diet. The overall body weight was comparable between the two groups. The experimental group had an increased lean body mass. The fat mass and relative fat mass developed later in life at was reduced in the pups which had received the diet with the phospholipid coated, larger lipid globules during their infancy and childhood, compared to pups which had received the control diet. The overall body weight was comparable between the two groups. The experimental group had an increased lean body mass.

These results demonstrate that the BMC and/or BMD in later life clearly is increased by an early in life diet with phospholipid coated lipid globules. It is concluded that food comprising lipid globules with an altered lipid architecture program and/or imprint the body early in life in such a way that later at life a healthier body composition has developed, with increased BMD and/or BMC, which prevents and/or reduces the risk for osteoporosis. Although the experiment 2 and 3 cannot be directly compared, the effects at day 98 are relatively higher in experiment 3, indicative for a further improved effect when the lipid globules are enlarged in size.

Interestingly, at the same time the development of fat mass (being not significantly different at day 42, the end of the diet intervention period) the fat mass and relative fat mass developed later in life was reduced in the pups which had received the diet with the phospholipid coated lipid globules during their infancy and childhood, compared to pups which had received the control diet.

Example 4

In parallel an experiment was performed wherein the effects of an IMF with standard vegetable lipid was compared with IMF wherein the lipid component comprises structured triglycerides with an increased amount of palmitic acid in the sn-2 position. From literature it is known that upon using such lipids, less free palmitic acid is formed, resulting in less formation of insoluble calcium palmitate, thereby increasing the bioavailability of calcium and palmitic acid. The experimental set up was similar as in example 3. The tested diets were based on AIN-93G comprising the same carbohydrate and protein component. The diet comprised 7% lipid, wherein diet 1 comprised the palm oil, coconut oil, rapeseed oil, sunflower oil, and high oleic acid sunflower oil. In diet 2 part about 70 wt % of the fat was Betapol™ 45 (Lipid Nutrition, The Netherlands) a lipid in which about 45% of the palmitic acid is esterified in the sn-2 position of the triglyceride instead of the 7.5% typical for vegetable fats. The fatty acid composition of the diets is very similar, see Table 7.

TABLE 7

Fatty acid composition of the diets

|  | Diet 1, Control IMF | Diet 2, betapol |
|---|---|---|
| C12:0 | 11.5 | 11.5 |
| C14:0 | 4.6 | 4.3 |
| C16:0 | 17.1 | 17.1* |
| C18:0 | 3.0 | 2.8 |
| C18:1 n-9 | 36.0 | 38.7 |
| C18:2 n-6 (LA) | 14.0 | 14.0 |
| C18:3 n-3 (ALA) | 2.6 | 2.6 |
| Others | 11.2 | 9.3 |

*Increased fraction position at the sn-2 position of the lipid.

Results are shown in table 8. The diet comprising more palmitic acid on the sn-2 position increased body weight, lean body mass and fat mass on day 42. These effects were maintained later in life. An increase later in life on bone mineral content and bone mineral density was also observed. This differs from the effect of the phospholipid coated lipid globules of example 2 and 3, where a concomitant decrease in fat mass and no effect on overall body weight was observed later in life and wherein the direct diet effects (i.e. effects on day 42) on body weight, lean body mass and fat mass were much less.

TABLE 8

Bone mineral Content, Bone Mass density, Fat mass and relative fat mass.

|  | Day | Diet 1 | Diet 2 |
|---|---|---|---|
| Body weight g | 42 | 23.8 (0.55) | 24.7 (0.63) |
| Mean (s.e.) | 70 | 26.8 (0.72) | 30.3 (0.86)* |
|  | 98 | 28.1 90.67) | 31.8 (1.49)* |
| Lean body mass g | 42 | 18.0 (0.81) | 20.7 (0.41) |
| Mean (s.e.) | 70 | 20.0 (0.33) | 22.7 (0.54)* |
|  | 98 | 21.3 90.48) | 22.9 (0.77)* |
| Bone mineral content g | 42 | 0.410 (0.013) | 0.411 (0.010) |
| Mean (s.e.) | 70 | 0.504 (0.008) | 0.535 (0.014) |
|  | 98 | 0.557 (0.016) | 0.583 (0.18) |
| Bone mineral density g/cm2 | 42 | 0.045 (0.001) | 0.046 (0.001) |
| Mean (s.e.) | 70 | 0.053 (0.001) | 0.054 (0.001) |
|  | 98 | 0.053 (0.001) | 0.055 (0.001) |
| Fat mass g | 42 | 3.7 (0.22) | 4.3 (0.14) |
| Mean (s.e) | 70 | 5.1 (0.22) | 5.9 (0.44) |
|  | 98 | 5.1 (0.23) | 5.4 (0.62) |
| Fat % of body weight | 42 | 17.0 (0.39) | 17.6 (0.57) |
| Mean (s.e.) | 70 | 20.3 (0.57) | 20.4 (0.91) |
|  | 98 | 19.2 (0.78) | 18.8 (1.33) |

*$p < 0.05$

Example 5

Infant Nutrition with Phospholipid Coated Lipid Globules

An infant formula comprising per kg powder 4810 kcal, 255 g lipid, 533 g digestible carbohydrates, 58 g non-digestible oligosaccharides (galacto-oligosaccharides and long chain fructo-oligosaccharides in a weight ratio of 9/1), 96 g protein, and vitamins, minerals, trace elements as known in the art.

The lipid composition is such that 0.57 wt. % of the lipid is composed of phospholipids. The composition comprises about 0.17 wt. % glycosphingolipids based on total lipid. The composition comprises about 0.006 wt. % cholesterol based on total lipids. As a source of phospholipids, glycosphingolipids and cholesterol SM-2 powder (Corman, Goé, Belgium) is used. About 97-98% of the lipid is vegetable lipid, the rest being milk fat, fish oil and microbial oil. The amount of LC-PUFA is about 0.64 wt. % based on total fatty acids. The LA/ALA ratio is 5.2.

The IMF was prepared in a process similar to the experimental diet 3 of example 1B. The volumetric mode diameter was below 1 μm. The volume % of lipid globules with a size between 2 and 12 m was below 45% based on total lipid volume. The lipid globules were covered by a layer of phospholipids.

The invention claimed is:

1. A method of increasing bone mass density and/or increasing bone mineral content, comprising administering to a human subject between 0 and 36 months of age at risk of developing osteoporosis or in need of enhancement of bone formation and/or bone mass maximation, a composition comprising:
   (a) 10 to 50 wt. % of vegetable lipids, based on dry weight of the composition,
   (b) 1.0 to 10 wt. % of phospholipids, based on total lipid,
   (c) glycosphingolipids, and
   (d) cholesterol,
   wherein the lipids comprise at least 16 wt. % palmitic acid based on total fatty acids of the composition, and
   wherein the vegetable lipids and the phospholipids are in lipid globules with a core comprising said vegetable lipids and a coating comprising said phospholipids lipids.

2. The method according to claim 1, wherein the lipid globules have:
   i) a volume-weighted mode diameter below 1.0 μm, and
   ii) a diameter of 2 to 12 μm in an amount of at less than 45 volume % based on total lipid.

3. The method according to claim 2, wherein the lipid globules have:
   (i) a volume-weighted mode diameter in the range of 0.3-0.6 μm, and
   (ii) a size distribution wherein more than 55 volume % of the lipid globules has a diameter of less than 2 μm.

4. The method according to claim 1, wherein the lipid globules have:
   (i) a volume-weighted mode diameter above 1.0 μm, and
   (ii) a diameter of 2 to 12 μm in an amount of at least 45 volume % based on total lipid.

5. The method according to claim 4, wherein the lipid globules have:
   (i) a volume-weighted mode diameter in the range of 1.0-10 μm, and/or
   (ii) diameter of 2 to 12 μm in an amount of at least 55 volume % based on total lipid.

6. The method according to claim 1, wherein the phospholipids are derived from milk lipids.

7. The method according to claim 1, wherein the composition comprises 1.0 to 25 wt. % of polar lipids based on total lipids, wherein polar lipids are the sum of phospholipids, glycosphingolipids and cholesterol.

8. The method according to claim 1, wherein the composition has a fatty acid profile with a linoleic acid to alpha-linolenic acid weight ratio between 4 and 7.

9. The method according to claim 1, wherein over 75 wt. % of the palmitic acid is in the sn-1 or sn-3 position.

10. The method according to claim 1, wherein the composition further comprises least one lipid selected from the group consisting of fish oil, marine oil, algal oil, fungal oil and microbial oil.

11. The method according to claim 1, wherein the composition further comprises non-digestible oligosaccharides.

12. A method of treating and/or preventing osteoporosis and/or osteopenia, comprising administering to a human subject between 0 and 36 months of age at risk of developing osteoporosis and/or ostopenia a composition comprising:
   (a) 10 to 50 wt. % of vegetable lipids, based on dry weight of the composition,
   (b) 1.0 to 10 wt. % of phospholipids, based on total lipid,
   (c) glycosphingolipids, and
   (d) cholesterol,
   wherein the lipids comprise at least 16 wt. % palmitic acid based on total fatty acids of the composition, and
   wherein the vegetable lipids and the phospholipids are in lipid globules with a core comprising said vegetable lipids and a coating comprising said phospholipids.

13. The method according to claim 12, wherein the lipid globules have:
   i) a volume-weighted mode diameter below 1.0 μm, and
   ii) a diameter of 2 to 12 μm in an amount of at less than 45 volume % based on total lipid.

14. The method according to claim 12, wherein the lipid globules have:
   (i) a volume-weighted mode diameter above 1.0 μm, and
   (ii) a diameter of 2 to 12 μm in an amount of at least 45 volume % based on total lipid.

15. The method according to claim 5, wherein the lipid globules have a volume-weighted mode diameter between 4.0 μm and 8.0 μm.

16. The method according to claim 1, wherein the composition further comprises gangliosides.

17. The method according to claim 1, wherein the increasing bone mass density and/or increasing bone mineral content is observed when the human subject has an age above 5 years.

* * * * *